(12) United States Patent
Lopez et al.

(10) Patent No.: US 9,918,462 B2
(45) Date of Patent: Mar. 20, 2018

(54) METHOD FOR WARMING A TISSUE OR ORGAN FOR IMPLANTATION

(75) Inventors: George-Antoine Lopez, Ecully (FR); Silvina Ramella Virieux, Lyons (FR); Marcos Juan Net Abraham, Barcelona (ES)

(73) Assignee: GROUPE IGL, Lissieu (FR)

( * ) Notice: Subject to any disclaimer, the term of this patent is extended or adjusted under 35 U.S.C. 154(b) by 307 days.

(21) Appl. No.: 14/114,399

(22) PCT Filed: Apr. 6, 2012

(86) PCT No.: PCT/FR2012/050758
§ 371 (c)(1),
(2), (4) Date: Nov. 21, 2013

(87) PCT Pub. No.: WO2012/150392
PCT Pub. Date: Nov. 8, 2012

(65) Prior Publication Data
US 2014/0080111 A1    Mar. 20, 2014

(30) Foreign Application Priority Data
May 2, 2011 (FR) ...................................... 11 53745

(51) Int. Cl.
*A01N 1/02* (2006.01)
(52) U.S. Cl.
CPC .................................. *A01N 1/0226* (2013.01)
(58) Field of Classification Search
None
See application file for complete search history.

(56) References Cited

U.S. PATENT DOCUMENTS

| 4,981,681 A * | 1/1991 | Tosti ................... A61K 9/0014 424/78.05 |
| 5,145,771 A | 9/1992 | Lemasters et al. |
| 6,641,992 B2 * | 11/2003 | Lopez .................... A01N 1/02 435/1.3 |
| 6,727,210 B1 * | 4/2004 | Perdew, Jr. .......... A61K 8/0208 510/130 |
| 6,994,654 B2 * | 2/2006 | Sakaguchi ............ F02D 31/005 477/110 |
| 9,149,493 B2 * | 10/2015 | Zanarotti ............... A61K 45/06 |

FOREIGN PATENT DOCUMENTS

| EP | 1178726 A1 | 2/2002 |
| EP | 1997374 A2 | 12/2008 |
| WO | WO-199505076 A1 | 2/1995 |
| WO | WO-199835551 A1 | 8/1998 |

OTHER PUBLICATIONS

European Patent Office, International Search Report dated Nov. 15, 2012 for International Application No. PCT/FR2012/050758 in the French and English languages (6 pgs).
Y. Neuzillet, et al., "Effects of the Molecular Weight of Peg Molecules (8, 20 and 35 KDA on Cell Function and Allograft Survival Prolongation in Pancreatic Islets Transplantation", Transplantation Proceedings, Sep. 2006, vol. 38, No. 7 (pp. 2354-2355).

* cited by examiner

*Primary Examiner* — Blaine Lankford
(74) *Attorney, Agent, or Firm* — Harris Beach PLLC

(57) ABSTRACT

Extracellular organ or tissue rinsing solution, comprising calcium, PEG with a molecular weight of 35 000 at a concentration of at least 4 g/l, and potassium at a concentration of greater than or equal to 1, but less than 10 mmol/l.

9 Claims, 7 Drawing Sheets

METHOD FOR WARMING A TISSUE OR ORGAN FOR IMPLANTATION

CROSS-REFERENCE TO RELATED APPLICATIONS

This application is a national stage application under 35 U.S.C. § 371 of PCT Application No. PCT/FR2012/050758, filed Apr. 6, 2012, which claims priority to and the benefit of French Application No. 1153745 filed on May 2, 2011, which are incorporated herein by reference in their entirety.

The invention aims at a solution for rinsing organs or grafts such as, but not limited to, the kidney, liver, heart, as well as tissues such as veins, arteries, valves, vessels . . . . It also aims at a method for rinsing said graft or tissues before revascularization.

The invention is more particularly described in relation with a kidney rinsing during a transplant procedure.

Kidney transplantation is, by far, the most common organ transplant. It is performed on patients with end stage renal disease. It is today the treatment of choice for renal impairment since it is better than dialysis in terms of patient quality of life.

Following a kidney transplantation, a number of immunological and non-immunological complications may occur which may, among other things, compromise the functional prognosis of the graft. Apart from the problems raised by the risk of transplant rejection, ischemic nephropathy presents a major complication associated with the transplant procedure. Indeed, all the steps of the kidney transplant procedure are as many circumstances providing an ischemic stress. Understanding the physiological events involved in ischemia-reperfusion and leading to possible therapies is therefore critical.

A number of strategies are in place to prevent ischemia-reperfusion injury during transplantation, among others, the cooling of grafts (at +4° C.) with the use of preservative solutions and in particular the UW solution. This strategy, although widely used, has drawbacks. Cold storage is likely to cause cell and tissue damage. The UW intracellular-like preservation solution (University of Wisconsin), also known under trademark BELZER-VIASPAN, contains a high potassium concentration (125 mM). Now, during the ischemic period, grafts release a number of catabolites (e.g. endothelin . . . ). They may further accumulate large quantities of this ion (K+) and of these catabolites, which may cause lesions in the recipient during the reperfusion phase. Moreover, hyperkalemia of the graft is likely to cause disturbances of the recipient's heart rate.

It is therefore essential to thoroughly rinse the organ before its vascularization in order to eliminate an excess of residual potassium in the graft, and also all the cellular metabolism degradation products that have accumulated during the preservation phase and which will take part in the activation of the cascade of events leading to reperfusion damage.

A solution for the preservation and rinsing of organs and tissues referred to as the "Carolina rinse" is known from document U.S. Pat. No. 5,145,771. This solution is based on adenosine and also contains sodium, calcium, magnesium and less than 6 MEQ/L of potassium.

Document EP-A-713 363 describes an improvement to the previous solution in that it also contains glycine.

Document EP-A-1 178 726 describes an extracellular-like organ preservation solution containing calcium and PEG of molecular weight 35,000. It is not envisaged to use the solution for rinsing. Further, the described PEG concentrations range from 0.01 to 5 millimoles per liter, that is, between 0.35 g/l and 175 g/l. The preferred values are lower than 1 millimole (35 g/l), advantageously equal to 0.03 millimole/liter, or 1 g/l. Similarly, the potassium concentration in the described formulation ranges from 10 to 40 millimoles.

The problem that the invention aims at solving is to develop a new rinsing solution enabling to optimize the warming phase of the graft during its implantation in the recipient, when used after cold preservation and prior to revascularization.

The Applicant has observed that quite surprisingly, the implementation of a concentration of PEG of molecular weight 35,000 at least 4-fold greater than the advantageous concentration described in document EP-A-1 178 726 combined with a low concentration of potassium could make the preservation solution described usable for the rinsing of organs.

In other words, the invention aims at an extracellular-like organ and tissue rinsing solution, containing calcium, PEG of molecular weight 35,000 at a concentration of at least 4 g/l, advantageously 5 g/l and potassium, at a concentration greater than or equal to 1 mmol/L, but smaller than 10 mmol/L.

The solution is extracellular-like in that it contains more Na+ than K+.

Another characteristic is that the calcium concentration ranges between 0.1 and 2, and is advantageously equal to 1.3 mmol/L.

According to a preferred embodiment, the rinsing solution of the invention contains sodium at a concentration ranging between 10 and 150, advantageously equal to 20 mmol/L.

According to another preferred embodiment, the rinsing solution of the invention contains potassium, at a concentration advantageously ranging between 1 and 9, and advantageously equal to 5 mmol/L.

The rinsing solution of the invention also advantageously contains:
  raffinose pentahydrate at a concentration ranging between 20 and 40, advantageously equal to 30 mmol/L,
  lactobionate at a concentration ranging between 70 and 140, advantageously equal to 100 mmol/L.

Besides, the pH of the rinsing solution of the invention advantageously ranges between 6.5 et 8, preferably equal to 7.4.

The osmolarity of the solution ranges between 290 and 330, and is advantageously equal to 320 mosm/kg.

In a preferred embodiment, the composition of the rinsing solution of the invention is the following:

| | |
|---|---|
| $CaCl_2, 2H_2O$ (mmol/L) | 1.3 |
| $KH_2PO_4$ (mmol/L) | 5 |
| $NaH_2PO_4$ (mmol/L) | 20 |
| $MgSO_4, 7H_2O$ (mmol/L) | 5 |
| Lactobionate (mmol/L) | 100 |
| Raffinose (mmol/L) | 30 |
| PEG (PM 35,000) (g/l) | 5 |
| pH | 7.4 |
| osmolarity (mosm/kg) | 320 |

The invention also aims at a method for rinsing organs or tissues before implantation in the patient, according to which the organ or tissue is rinsed with the solution described hereabove.

The invention and the resulting advantages will well appear from the following embodiments, in relation with the accompanying drawings.

1/ PREPARATION OF THE RINSING SOLUTION OF THE INVENTION

A solution having the following composition and characteristics is prepared by mixing the ingredients (for 1 liter):

| | |
|---|---|
| $CaCl_2$, $2H_2O$ (mmol/L) | 1.3 |
| $KH_2PO_4$ (mmol/L) | 5 |
| $NaH_2PO_4$ (mmol/L) | 20 |
| $MgSO_4$, $7H_2O$ (mmol/L) | 5 |
| Lactobionate (mmol/L) | 100 |
| Raffinose (mmol/L) | 30 |
| PEG 35M (g/l) | 5 |
| pH | 7.4 |
| osmolarity (mosm/kg) | 320 |

In section 2/ and the corresponding drawings, this solution is referred to as SB PEG 5.

2/ CASE OF LIVER IN VIVO a/ Preparation of the Solutions

In addition to the rinsing solution of the invention, the following three solutions are prepared:

SB PEG 1 (for 1 Liter)

| | |
|---|---|
| $CaCl_2$, $2H_2O$ (mmol/L) | 1.3 |
| $KH_2PO_4$ (mmol/L) | 5 |
| $NaH_2PO_4$ (mmol/L) | 20 |
| $MgSO_4$, $7H_2O$ (mmol/L) | 5 |
| Lactobionate (mmol/L) | 100 |
| Raffinose (mmol/L) | 30 |
| PEG 35M (g/l) | 1 |
| pH | 7.4 |
| osmolarity (mosm/kg) | 320 |

SB (for 1 Liter)

| | |
|---|---|
| $CaCl_2$, $2H_2O$ (mmol/L) | 1.3 |
| $KH_2PO_4$ (mmol/L) | 5 |
| $NaH_2PO_4$ (mmol/L) | 20 |
| $MgSO_4$, $7H_2O$ (mmol/L) | 5 |
| Lactobionate (mmol/L) | 100 |
| Raffinose (mmol/L) | 30 |
| pH | 7.4 |
| osmolarity (mosm/kg) | 320 |

RLS (Ringer Lactate Solution)
For 100 ml:

| | |
|---|---|
| Sodium chloride | 600 mg |
| Potassium chloride | 40 mg |
| Calcium chloride | 27 mg |
| Sodium lactate | 312 mg |
| osmolarity (mosm/l) | 277 |
| pH | from 5 to 7 | b/ Experimental Conditions

The liver is removed and washed with a UW solution (50 ml) at 4° C. The organ is then preserved in static fashion in the same UW solution (100 ml) for 24 h at 4° C. The liver is then washed with each of the 4 above solutions. The various parameters are then measured on the liver reperfused under normal temperature conditions at 37° C. for 2 h.

c/ Bile Production

Figure 1:
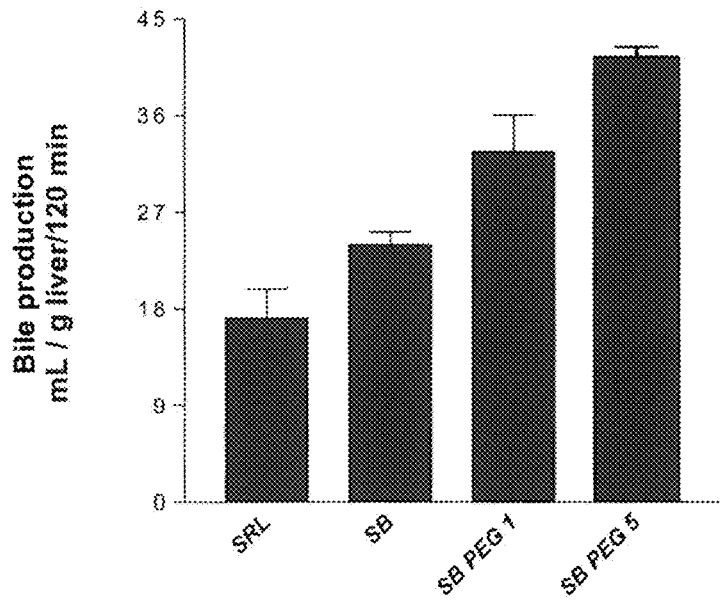
FIG. 1 is a graphical representation of the production of bile by a reperfused liver previously washed with the solution of the invention.

As shown in FIG. 1, the production of bile after 120 minutes of reperfusion is improved when the liver is previously washed with the solution of the invention (SB PEG 5) as compared with solutions of prior art.

d/ Vascular Resistance

Figure 2:
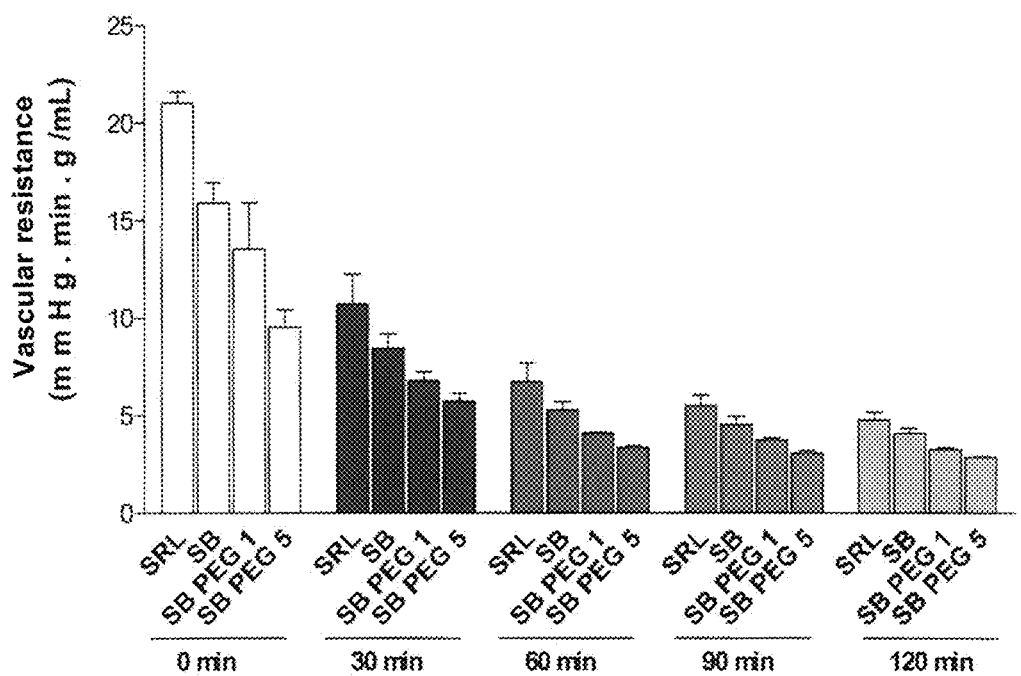
FIG. 2 is a graphical representation of the vascular resistance of a reperfused liver previously washed with the solution of the invention.

As shown in FIG. 2, the presence of PEG at 5 g/l in the solution of the invention enables to decrease the vascular resistance as compared with the same solution containing PEG at 1 g/l.

e/ Endothelium Protection e NOS

Figure 3:
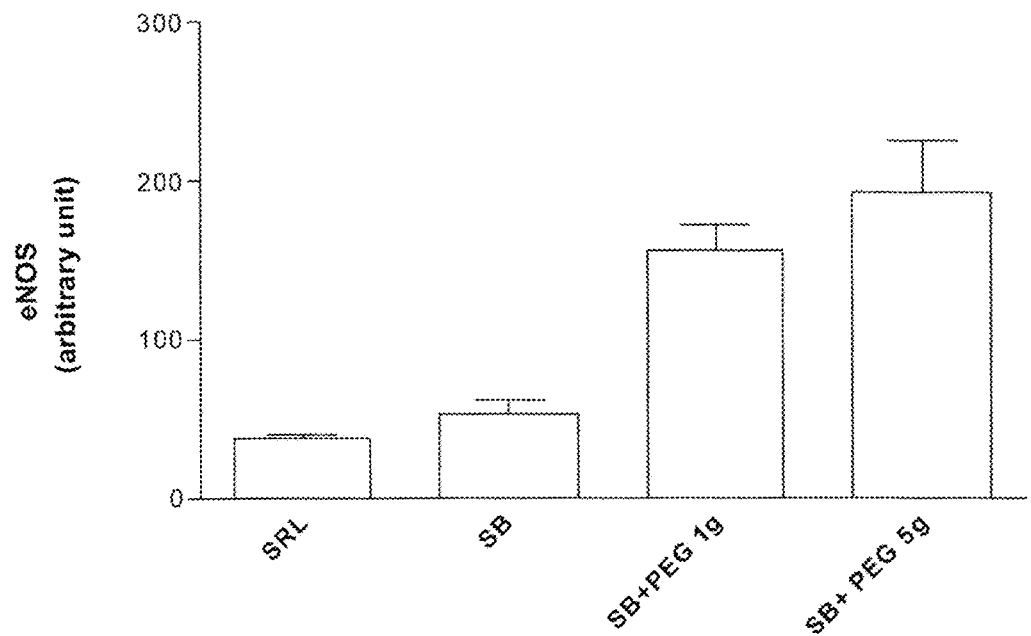
FIG. 3 is a graphical representation of the activity of endothelial nitric oxide synthase (e NOS) in a reperfused liver previously washed with the solution of the invention.

As shown in FIG. 3, the rinsing solution of the invention enables to improve the activity of endothelial nitric oxide synthase (e NOS).

Lipid Peroxidation

Figure 4:
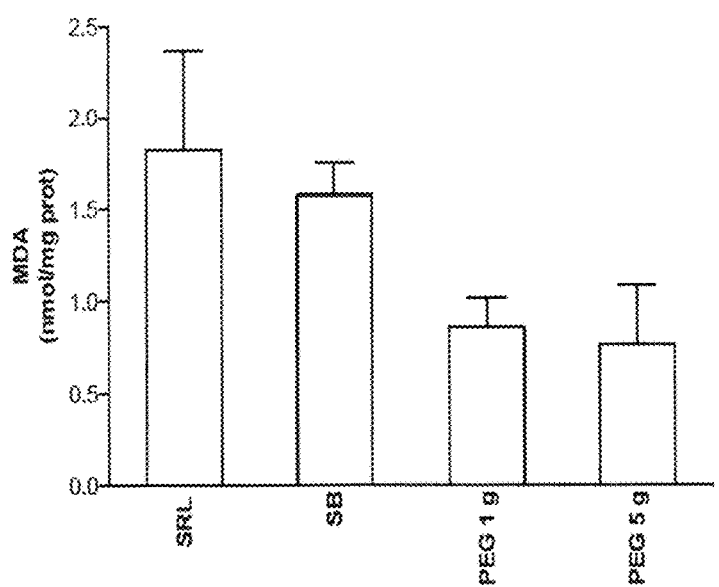
FIG. 4 is a graphical representation of lipid peroxidation in a reperfused liver previously washed with the solution of the invention.

As shown in FIG. 4, the rinsing solution of the invention enables to slightly decrease lipid peroxidation and thus to improve the preservation of the endothelium. It has no adverse effect.

f/ Production of Cytoprotective HSP (Heat Shock Protein)

Figure 5:
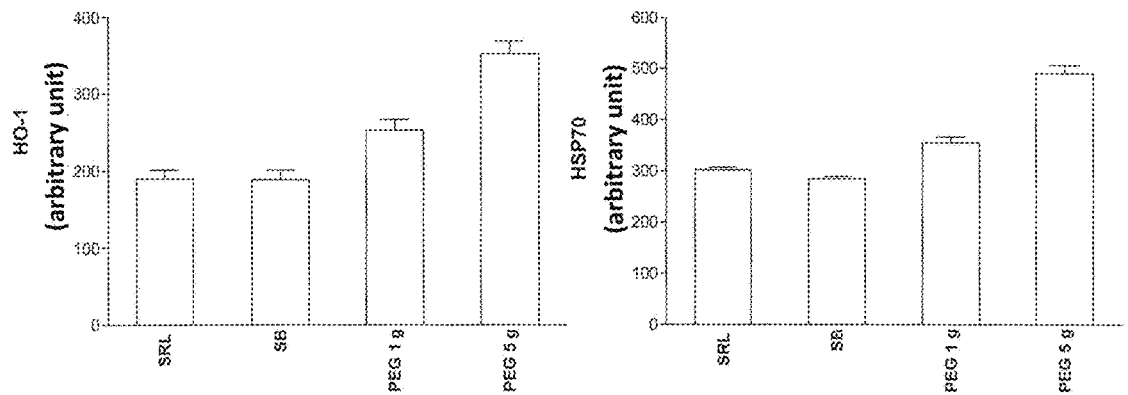
FIG. 5 is a graphical representation of the production of cytoprotective HSP (Heat Shock Protein) induced by a reperfused liver previously washed with, the solution of the invention.

As shown in FIG. 5, the production of cytoprotective HSP (Heme Oxygenase-1 and HSP 70) is induced by the presence of PEG35. This effect is even more obvious at 5 g/l of PEG.

3/ CASE OF THE KIDNEY, IN VIVO EXPERIMENTS

Wistar rats weighing between 180 and 280 g are used, with free access to food and water. The study is conducted on 25 rats randomly allocated to 5 experimental groups:

→Control group: graft-free rats are used for establishing the physiological parameters.

→2 h no-rinse group: kidney grafts are not rinsed prior to implantation in the recipient, they are revascularized for 2 h after transplantation.

→6 h no-rinse group: kidney grafts are not rinsed prior to implantation in the recipient, they are revascularized for 6 h after transplantation.

→2 h rinse group: kidneys are rinsed prior to transplantation and are revascularized for 2 h after transplantation.

→6 h rinse group: kidneys are rinsed prior to transplantation and are revascularized for 6 h after transplantation.

After their removal, kidneys from all groups, except the control group, are stored in the UW solution at 4° C. for 18 h. They are subsequently transplanted into recipient animals.

The rinsing solution used is the above-described solution of the invention.

Figure 6:
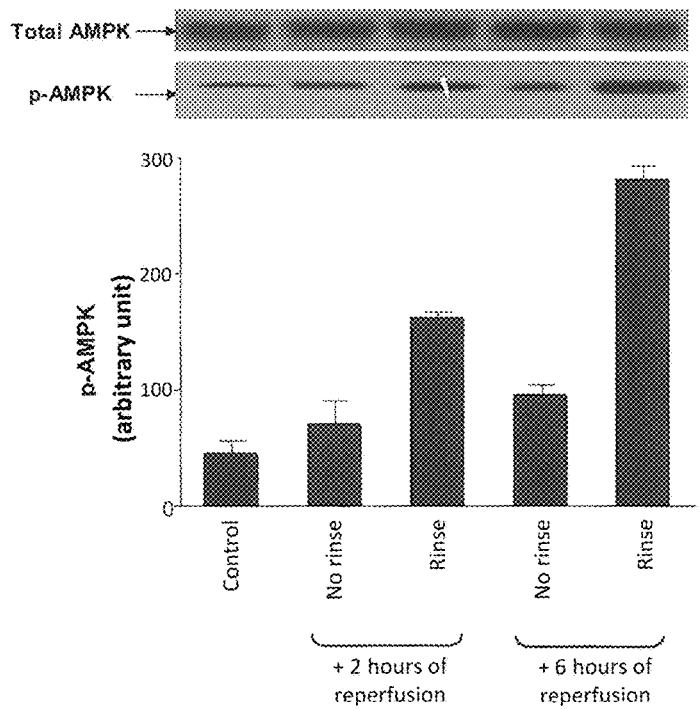
FIG. 6 is a graphical representation of the determination of phosphorylated AMP kinase in a transplanted kidney previously washed with the solution of the invention.

The transplanted kidneys are collected and stored at −20° C. The tissues are used to perform the following assays:

a/ Phosphorylated AMP Kinase (p-AMPk, an Enzyme Involved in Energy Metabolism) (FIG. 6)

Figure 7:
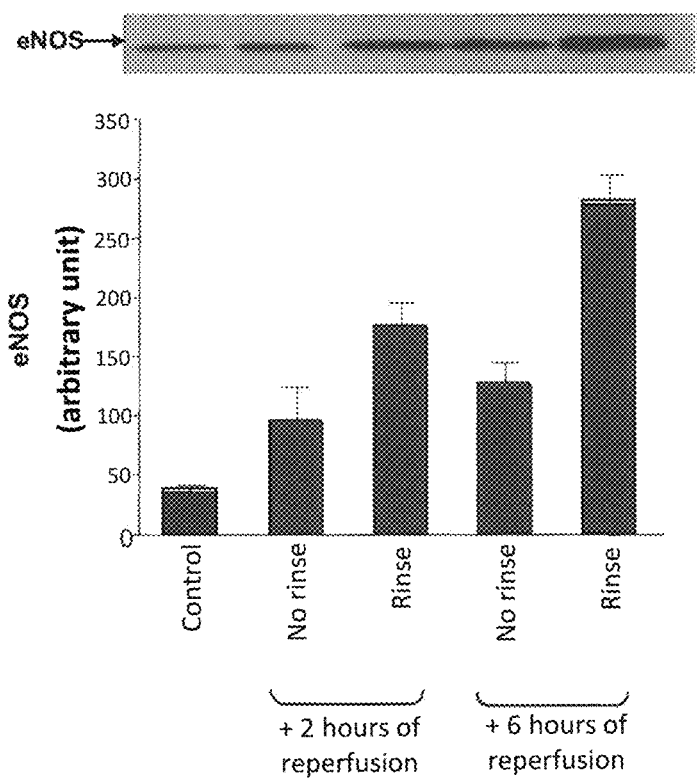
FIG. 7 is a graphical representation of the determination of endothelial NO synthase in a transplanted kidney previously washed with the solution of the invention.

The electrophoretic profile shows the same rate of total AMPk for all experimental groups. However, the phosphorylation rate of this enzyme varies according to experimental conditions. The two no-rinse groups have no statistically significant difference with respect to the control group. It should however be noted that rinsing significantly increases ($p<0.05$) the AMPk phosphorylation by opposition to not rinsing.

b/ Endothelial NO Synthase (eNOS, a Constitutive Enzyme Involved in NO Synthesis) (FIG. 7)

Figure 8:
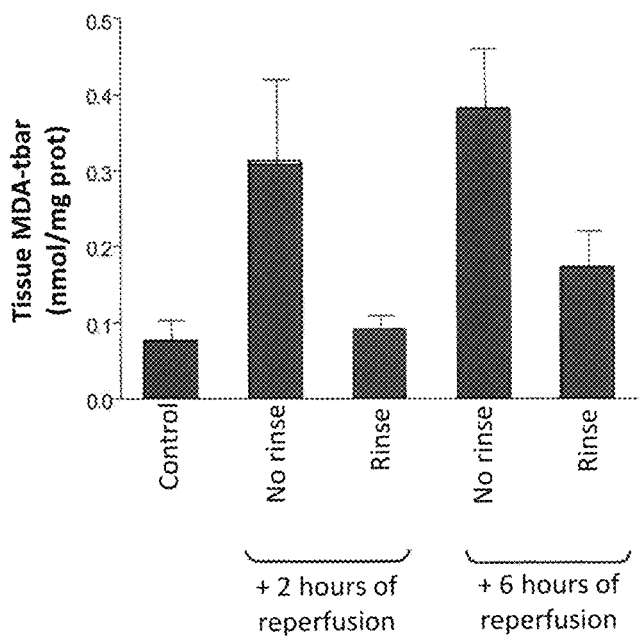
FIG. 8 is a graphical representation of the determination of malondialdehyde in a transplanted kidney previously washed with the solution of the invention.

The effect of rinsing on endothelial nitric oxide synthase is studied in relation with β-actin. This protein has a concentration which does not vary between samples. It is thus suitable as an internal control. It can be observed that endothelial nitric oxide synthase increases under the effect of rinsing and of the duration of reperfusion. Statistical analysis demonstrates a significant difference ($p<0.05$) between, on the one hand, 2 h and 6 h rinse groups, and, on the other hand, the control group. Besides, after 6 h of reperfusion, endothelial nitric oxide synthase is higher in the rinse group than in the no-rinse group ($p<0.05$).

c/ Oxidative Stress Decrease determination of malondialdehyde (MDA-TBAR, a product of lipid peroxidation) (FIG. 8)

Figure 9:
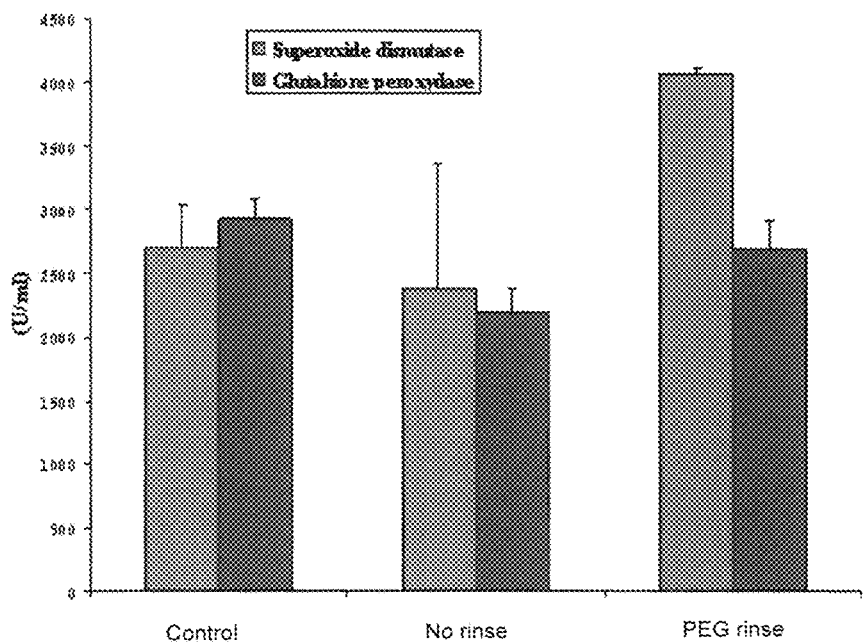
FIG. 9 is a graphical representation of the determination of superoxide dismutase and glutathione dismutase in a transplanted kidney previously washed with the solution of the invention.

It should be noted that the highest concentrations of MDA-TBAR are found in the 2 h and 6 h no-rinse groups. Rinsing the kidneys prior to transplantation enables to significantly decrease ($p<0.05$) lipid peroxidation as compared with the no-rinse group.

determination of superoxide dismutase and glutathione dismutase (FIG. 9)

Figure 10:
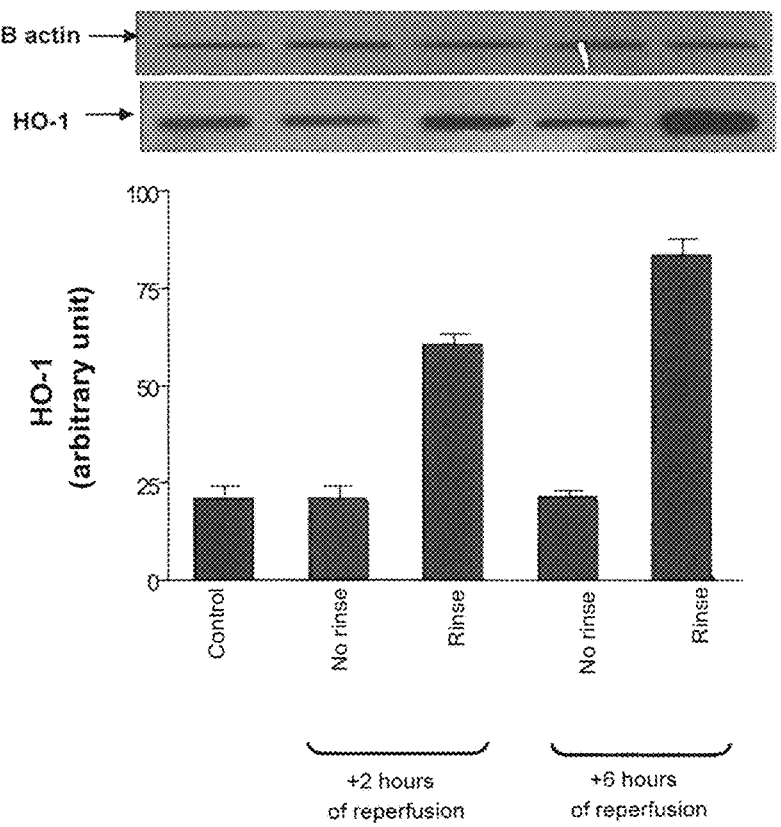
FIG. 10 is a graphical representation of the determination of heme oxygenase-1 in a transplanted kidney previously washed with the solution of the invention.

As shown in FIG. 9, the superoxide dismutase and glutathione dismutase concentrations increase in the transplanted kidney that has been rinsed by the solution of the invention, which characterizes an oxidative stress decrease.

d/ HSP Protein: Heme Oxygenase-1 (HO-1) (FIG. 10)

The variation in heme oxygenase-1 between groups is determined in relation to (β-actin. In the two no-rinse groups, the presence of heme oxygenase-1 is less significant ($p<0.05$) than in the rinse groups for the different durations. The production of cytoprotective HSP (Heme Oxygenase-1) is induced by the presence of PEG35 at 5 g/l.

e/ Endoplasmic Reticulum Stress Markers

The endoplasmic reticulum is an intracellular organelle of complex structure which forms a membranous network extending from the nucleus to the cell membrane. It provides an optimal environment for the maturation and assembly of native proteins. During this process, quality control occurs at the transcriptional, translational and conformational levels. Newly synthesized proteins must be perfectly folded to acquire their functionality.

One of the consequences of ischemia or oxidative stress is a disruption of the processes of protein maturation and folding in the endoplasmic reticulum. In these circumstances, they will not be transported to their final destination in the cell and will eventually be degraded by proteasomes. However, when they are produced in excess, misfolded proteins cannot all be degraded and will eventually accumulate in the lumen of the endoplasmic reticulum. This situation induces endoplasmic reticulum stress, causing the cell to activate a particular adaptive response called UPR (for "Unfolded Protein Response"). This response is characterized by an overall reduction of protein synthesis via translational block, an increase in the proteasomal degradation activity and an increase in the enzymatic capabilities for protein maturation. However, if this adaptive process fails and the stress is prolonged, the cell then activates pathways inducing programmed cell death.

Samples of tissues after 2 h and 6 h of graft revascularization are taken for the determination of the following markers:

Activating transcription factor-6 (ATF-6) (FIG. 10)

Figure 11:
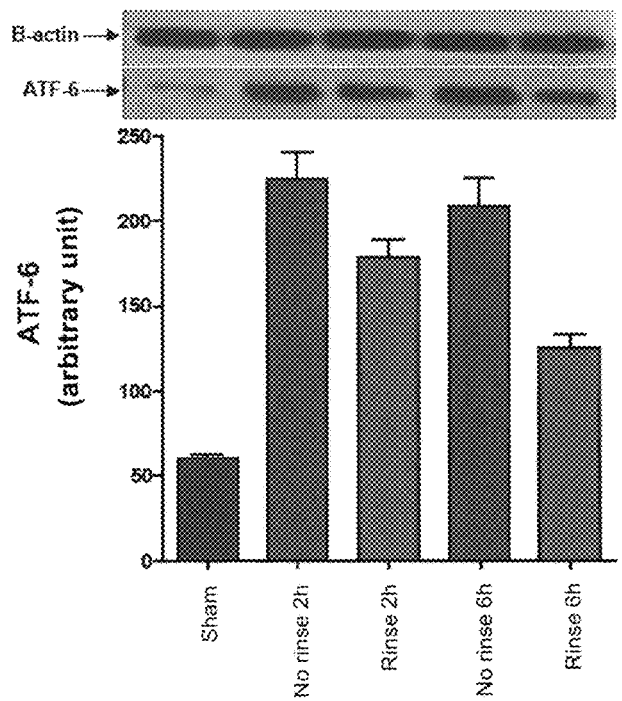
FIG. 11 is a graphical representation of the determination of the Activating Transcription Factor-6 (ATF-6) in a transplanted kidney previously washed with the solution of the invention.

Phosphorylated and total protein Kinase RNA-like endoplasmic reticulum kinase (p-PERK) (FIG. 11)

Figure 12:
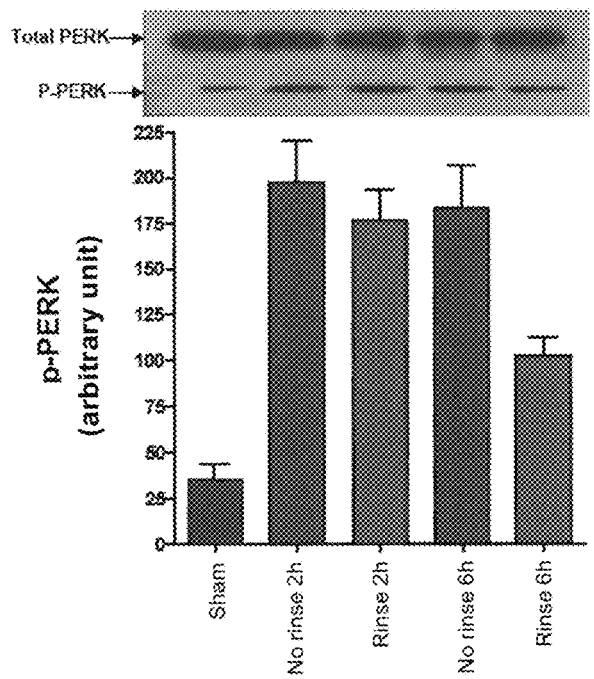
FIG. 12 is a graphical representation of the determination of the Phosphorylated and total protein Kinase RNA-like endoplasmic reticulum kinase (p-PERK) in a transplanted kidney previously washed with the solution of the invention.

X-box binding protein-1 (XBP-1) (FIG. 12)

Figure 13:
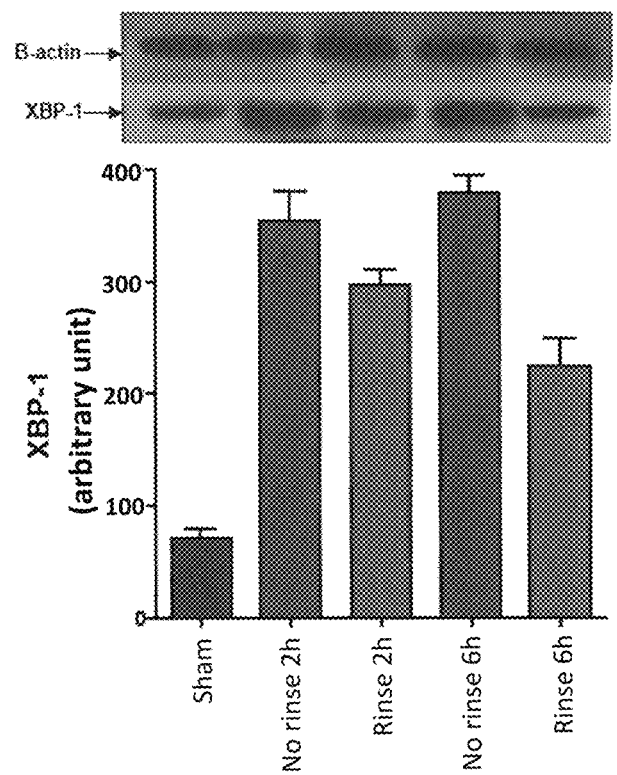
FIG. 13 is a graphical representation of the determination of the X-box binding protein1 (XBP-1) in a transplanted kidney previously washed with the solution of the invention.
Figure 14:
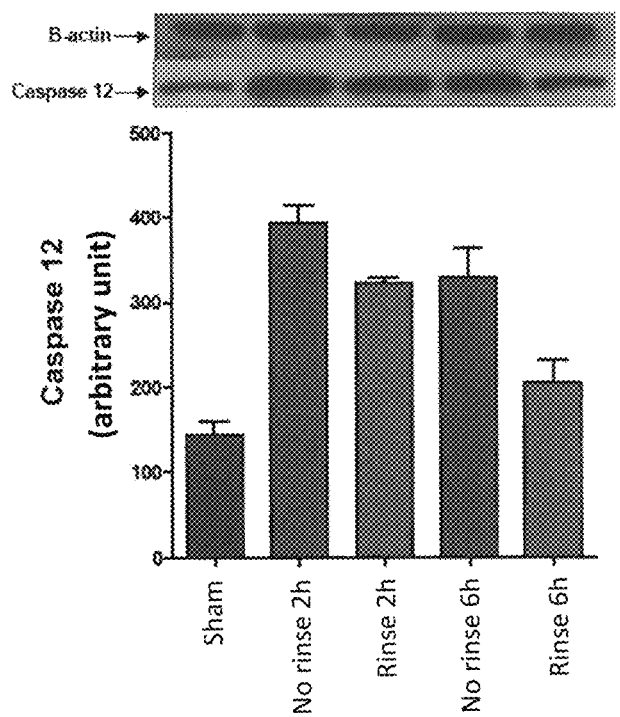
FIG. 14 is a graphical representation of the determination of Caspase-12 (Casp 12) in a transplanted kidney previously washed with the solution of the invention.

Caspase-12 (Casp 12) (FIG. 13) It should be noted that the higher mediators for the UPR response can be found in the 2 h and 6 h no-rinse groups as compared with the rinse groups ($p<0.05$). The rinsing of kidneys prior to transplantation enables to significantly decrease endoplasmic reticulum stress.

Caspase 12 is an activator for apoptosis following endoplasmic reticulum stress. It can be observed that caspase 12 is more activated in no-rinse groups than in rinse groups ($p>0.05$).

As a summary, the results show that rinsing the kidney graft after cold preservation leads to:

→Endothelial nitric oxide synthase activation and increased nitric oxide release →An increase in the phosphorylation of AMPk →An increase in antioxidant capabilities (HO-1 and SOD) and a decrease in lipid peroxidation (MDA)

→A decrease in endoplasmic reticulum stress

The invention claimed is:

1. A method for warming a cold-preserved organ or a cold-preserved tissue prior to implantation of the organ or the tissue in a patient, comprising:

rinsing the organ or the tissue with a solution, wherein the solution comprises calcium, PEG of molecular weight 35,000 at a concentration of at least 4 g/l, and potassium at a concentration ranging between 1 and 9 mmol/L, wherein the rinsing is performed after cold preservation.

2. The method of claim 1, wherein the PEG concentration of the solution is 5 g/l.

3. The method of claim 1, wherein the calcium concentration of the solution ranges between 0.1 and 2 mmol/L.

4. The method of claim 1, wherein the solution further comprises sodium at a concentration ranging between 10 and 150 mmol/L.

5. The method of claim 1, wherein the potassium concentration of the solution is 5 mmol/L.

6. The method of claim 1, wherein the solution further comprises:
   raffinose pentahydrate at a concentration ranging between 20 and 40 mmol/L, and
   lactabionate at a concentration ranging between 70 and 140 mmol/L.

7. The method of claim 1, wherein the pH of the solution ranges between 6.5 and 8.

8. The method of claim 1, wherein the osmolarity of the solution ranges between 290 and 330 mosm/kg.

9. The method of claim 1, wherein the solution comprises:

| | |
|---|---|
| $CaCl_2$, $2H_2O$ (mmol/L) | 1.3 |
| $KH_2PO_4$ (mmol/L) | 5 |
| $NaH_2PO_4$ (mmol/L) | 20 |
| $MgSO_4$, $7H_2O$ (mmol/L) | 5 |
| Lactobionate (mmol/L) | 100 |
| Raffinose (mmol/L) | 30 |
| PEG (PM 35,000) (g/l) | 5 | and wherein the pH is 7.4 and the osmolarity is 320 mosm/kg.

\* \* \* \* \*